(12) United States Patent
Adams et al.

(10) Patent No.: US 11,806,278 B2
(45) Date of Patent: Nov. 7, 2023

(54) IMPLANTABLE INTRAOCULAR DRUG DELIVERY DEVICES

(71) Applicant: Qura, Inc., Framingham, MA (US)

(72) Inventors: Douglas P. Adams, Sudbury, MA (US); Amitava Gupta, Roanoke, VA (US)

(73) Assignee: Qura, Inc., Duxbury, MA (US)

( * ) Notice: Subject to any disclaimer, the term of this patent is extended or adjusted under 35 U.S.C. 154(b) by 362 days.

(21) Appl. No.: 17/272,053

(22) PCT Filed: Aug. 30, 2018

(86) PCT No.: PCT/US2018/048659
§ 371 (c)(1),
(2) Date: Feb. 26, 2021

(87) PCT Pub. No.: WO2020/046299
PCT Pub. Date: Mar. 5, 2020

(65) Prior Publication Data
US 2021/0322212 A1    Oct. 21, 2021

(51) Int. Cl.
*A61F 9/00*    (2006.01)
*A61F 2/16*    (2006.01)

(52) U.S. Cl.
CPC .......... *A61F 9/0017* (2013.01); *A61F 2/1694* (2013.01); *A61F 2210/0004* (2013.01); *A61F 2210/0014* (2013.01); *A61F 2250/0002* (2013.01); *A61F 2250/0068* (2013.01); *A61F 2250/0096* (2013.01)

(58) Field of Classification Search
CPC .................. A61F 2/1694; A61F 9/0017; A61F 2250/0068; A61F 2250/0001; A61F 2250/0096; A61F 2250/0002
See application file for complete search history.

(56) References Cited

U.S. PATENT DOCUMENTS

| 8,475,374 | B2 | 7/2013 | Irazoqui et al. |
| 9,078,613 | B2 | 7/2015 | Irazoqui et al. |
| 9,173,564 | B2 | 11/2015 | Choo et al. |
| 9,596,988 | B2 | 3/2017 | Irazoqui et al. |
| 9,662,021 | B2 | 5/2017 | Chow et al. |

(Continued)

FOREIGN PATENT DOCUMENTS

| WO | WO-2010000671 A1 * | 1/2010 | ............... A61B 3/16 |
| WO | 2013090886 A1 | 6/2013 | |

(Continued)

OTHER PUBLICATIONS

International Search Report and Written Opinion in International Patent Application No. PCT/US2018/048659 dated Dec. 20, 2018, 12 pages.

(Continued)

*Primary Examiner* — Javier G Blanco
(74) *Attorney, Agent, or Firm* — Smith Baluch LLP

(57) ABSTRACT

The present disclosure relates to the field of implantable intraocular drug delivery devices. In particular, the present disclosure relates to intraocular drug delivery devices integrated into a capsular tension ring ("CTR") that is designed for implantation in the capsule or the ciliary sulcus during a cataract extraction and intraocular lens implantation procedure.

11 Claims, 8 Drawing Sheets

(56) References Cited

U.S. PATENT DOCUMENTS

| | | |
|---|---|---|
| 10,044,227 B2 | 8/2018 | Chappell et al. |
| 10,426,341 B2 | 10/2019 | Choo et al. |
| 2006/0246112 A1 | 11/2006 | Snyder et al. |
| 2010/0016439 A1* | 1/2010 | Thomes .................. A61K 47/32 514/619 |
| 2010/0137694 A1 | 6/2010 | Irazoqui et al. |
| 2012/0238857 A1* | 9/2012 | Wong .................... A61F 2/1694 600/398 |
| 2013/0109779 A1 | 5/2013 | Argal et al. |
| 2014/0134607 A1 | 5/2014 | Lin et al. |
| 2014/0200424 A1 | 7/2014 | Etzkorn et al. |
| 2015/0100046 A1* | 4/2015 | Ambati ................ A61F 9/0017 604/892.1 |
| 2016/0223842 A1 | 8/2016 | Yun et al. |
| 2016/0235524 A1 | 8/2016 | Wortz et al. |
| 2016/0235587 A1 | 8/2016 | Kahook et al. |
| 2017/0164831 A1 | 6/2017 | Choo et al. |
| 2017/0209045 A1 | 7/2017 | Choo et al. |
| 2018/0035888 A1 | 2/2018 | Irazoqui et al. |
| 2018/0375382 A1 | 12/2018 | Chappell et al. |
| 2019/0175015 A1 | 6/2019 | Adams et al. |
| 2020/0237218 A1 | 7/2020 | Irazoqui et al. |
| 2021/0030529 A1 | 2/2021 | Adams et al. |
| 2021/0052783 A1 | 2/2021 | Adams et al. |
| 2021/0137379 A1 | 5/2021 | Fehr et al. |
| 2021/0169427 A1 | 6/2021 | Adams et al. |

FOREIGN PATENT DOCUMENTS

| | | | |
|---|---|---|---|
| WO | 2016160456 A1 | 10/2016 | |
| WO | 2017210316 A1 | 12/2017 | |
| WO | WO-2018078026 A1 * | 5/2018 | ............... A61B 3/16 |
| WO | 2020023036 A1 | 1/2020 | |
| WO | 2020160262 A1 | 8/2020 | |
| WO | 2020236139 A1 | 11/2020 | |

OTHER PUBLICATIONS

Kuno et al., "Recent advances in ocular drug delivery systems." Polymers 3.1 (2011): 193-221.

Mujeeb-u-Rahman et al., "Fabrication of patterned integrated electrochemical sensors." Journal of Nanotechnology 2015 (2015). 14 pages.

* cited by examiner

CTR 14

CTR 14A

CTR 13

Cionni 1

Cionni 2

CTS Ahmed

CBR 1E Nishi-Menapace

CBR 1F Nishi-Menapace

FC-CBR Dick

IMPLANTABLE INTRAOCULAR DRUG DELIVERY DEVICES

CROSS-REFERENCE TO RELATED APPLICATION(S)

This application is a U.S. national stage filing under 35 U.S.C. 371 of International Application No. PCT/US2018/048659, filed Aug. 30, 2018, and entitled "IMPLANTABLE INTRAOCULAR DRUG DELIVERY DEVICES," which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The necessity of a device or a vehicle to release drugs in the intraocular space (both in the anterior chamber and in the vitreous) has been apparent ever since it was recognized that intracorneal penetration of drugs delivered in the form of eye drops is less than 1%. A significant unsolved need therefore is to develop a vehicle to deliver drugs over the long term (e.g., 1 month to 5 years) that does not interfere with other physiological functions of the eye (e.g., image formation and processing, maintaining intraocular pressure, etc.)

Capsular Tension Rings In 1991, Hara and co-workers were the first to publish the idea of inserting an endocapsular ring into the capsular bag when implanting an intraocular lens ("IOL") to address one or more of these challenges. They used a closed ring made of soft silicone with a groove on its inner surface to receive the loops of an IOL. At about the same time, Nagamoto independently presented the concept of using an open ring made of rigid poly methyl methacrylate ("PMMA") in order to maintain the circular contour of the capsular bag and thus avoid deformation or decentration of soft intraocular lenses. Implantation of a PMMA ring in human eyes was first reported in 1993. This ring was produced by Morcher and marketed under the name 'capsular tension ring' ("CTR"). It carried characteristic eyelets at its ends for atraumatic insertion and better manipulation (see FIG. 1). It was soon discovered that in addition to providing additional support to a capsule with compromised zonules (i.e., zonular dehiscence), CTRs also prevented migration of lens epithelial cells and thus retarded the onset of posterior capsular opacification ("PCO"). The various CTR designs differ significantly in resilience as defined by the spring constant, ranging from 0.88 to 4.55 mN/mm. While softer rings cause less zonular stress during insertion, more rigid rings counteract fibrotic capsular bag contraction. Some studies reported that, in cadaver eyes, a 12.5-mm ring diameter was found most appropriate for the human capsular bag. Commercially available CTRs range from 12.5 mm to 13.5 mm in diameter when designed for implantation in the capsule, while those designed for implantation in the ciliary sulcus have larger diameters, ranging from 14.0 mm to 14.5 mm. They are selected so that they fit the capsular equator of the individual patient, or to provide a desired level of centrifugal force, depending on their expected function in a particular case. They are typically, though not always, ring shaped and the thickness of the ring ranges from 0.12 mm to 0.7 mm when made of PMMA.

FIGS. 1A-1I show photomicrographs of exemplary capsular tension rings marketed by Morcher. The standard Morcher CTR comes in three sizes based on uncompressed diameter: 12.3 mm (compresses to 10 mm, Morcher 14, used for axial length<24 mm); 13 mm (compresses to 11 mm, Morcher 14C, used for axial length of 24-28 mm); and 14.5 mm (compresses to 12 mm, Morcher 14A, used for axial length>28 mm, designed for implantation in the sulcus). The Henderson CTR7 (FC-CBR) from Morcher GmbH (shown in FIG. 1I), differs from the standard ring in that it has eight equally spaced indentations of 0.15 mm and an uncompressed diameter of 12.29 mm that is compressible to 11 mm. It has been reported that an advantage of the Henderson CTR is that it allows for easier removal of nuclear and cortical material while maintaining equal expansion of the capsular bag.

A number of clinical studies of the safety and efficacy of CTR in the human eye have been performed. In all cases, no evidence of lack of biocompatibility have been presented, including breach of the capsule, or excessive IOL decentration, dislocation or rotational displacement of the IOL.

There is a benefit for some patients to have an implanted sensor in one or both eyes, such an intraocular pressure sensor. This can be the case with subjects with, for example, pre-existing glaucoma, preexisting diabetes (DM), or other retinal diseases such as diabetic retinopathy. A recent meta-analysis of 47 studies by Zhao and colleagues reported a pooled relative risk of glaucoma of 1.48 in patients with diabetes compared to those without diabetes. In addition, there was an increasing relative risk of glaucoma that was positively associated with diabetes duration. Though elevated IOP alone is a significant risk factor for but is not diagnostic for glaucoma, diabetic patients had a pooled average increase in IOP of 0.09 mmHg for every 10 mg/dl increase in fasting glucose. An epidemiological study on Danish patients suffering from diabetes indicated a strong association between occurrence of Diabetes Mellitus and onset of glaucoma treatment among the entire Danish population.

Intraocular drug delivery Intraocular drug delivery has been under development worldwide over the last 46 years, beginning with the introduction of pilocarpine containing Ocusert, a conjunctival device for sustained release of pilocarpine for management of glaucoma. Extensive studies have been carried out on controlled and sustained release of drugs incorporated in gels or biodegradable cross-linked networks. The rate of drug delivery can be modulated over several orders of magnitude by controlled variation of the solubility properties and level of molecular or segmental organization of the polymer matrix in which the drug is incorporated.

FIG. 2 shows examples of existing intravitreal drug delivery systems for vitreoretinal diseases (reproduced from Kuno, N, et al. "Recent Advances in Ocular Drug Delivery Systems" in Polymers, 2011; 3: pp 193, adapted from Kuno, N.; Fujii, S. Biodegradable intraocular therapies for retinal disorders. *Drugs Aging* 2010, 27, 117-13).

Recently, the emergence of lipid-based nanocarriers has provided a viable means of enhancing the bioavailability of ophthalmic formulations. A number of these formulations have been found to be clinically active. A micellar nanocarrier targeted to retinal ganglion cells at risk due to glaucoma was described by Zhao, et al. Electronically actuated drug delivery systems for intraocular applications are less common and their development has had to wait for realization of wireless supply of electrical energy to the implant. For example, an electronically controlled drug delivery system employing a novel electrochemical pump was disclosed in 2007. A flexible iontophoretically driven ocular drug delivery system, designed for subconjunctival applications was described by Zhang, et al in 2016.

FIG. 3 illustrates a liposome based drug delivery formulation, which may be optimized for retention and delivery of both hydrophilic and hydrophobic drugs.

In all cases, long term stability of the drug or drug formulation in the depot is a concern. It is also important to decide whether a preserved or non-preserved drug formulation will be used in the device. Since drug delivery systems are now, in some instances, being designed to operate for more than three years, stability of the drug formulation becomes crucially important, as well as their sterility. Recent studies show that ophthalmic pharmaceutical formulations can be stable for two years or more.

SUMMARY OF THE DISCLOSURE

This disclosure, including the inventions herein, relates to intraocular implantable drug delivery devices, which in some embodiments are integrated with a circular or arcuate capsular tension ring. The capsular tension rings can be configured and adapted for implantation into the capsule of a patient during a cataract extraction and intraocular lens implantation procedure.

These implantable devices may also be implanted in the ciliary sulcus of the patient, if the capsule is too damaged to sustain the implant. The drug delivery devices may be completely enclosed by the CTR, they may be coupled to the side of (or external surface of) the CTR, or part of the drug delivery device can be partially inside and partially outside the CTR.

One aspect of the disclosure is an intraocular implant that includes an implantable intraocular drug delivery system integrated with a capsular tension ring, sized and configured for implantation into at least one of the capsule and the ciliary sulcus of humans and/or canines.

One aspect of the disclosure is an intraocular implant, comprising an implantable intraocular drug delivery system comprising at least one drug depot and at least one sensor, the sensor adapted to sense at least one of intraocular pressure, a drug that is part of a drug delivery program that is being administered to a patient, and a biomarker indicative of intraocular pressure or other disease state.

One aspect of the disclosure is a method of intraocular drug delivery, the method comprising: in a patient implanted with an implant that includes a drug delivery depot integrated with a capsular tension ring and at least one sensor; obtaining sensed information that is indicative of at least one of intraocular pressure, a drug being delivered to the patient, and a biomarker indicative of IOP or a disease state; transmitting the sensed information or processed sensed information to a remote device; performing at least some degree of analysis on the sensed information or processed sensed information; and making a decision whether or not to change some aspect of the patient's therapy or treatment.

DETAILED DESCRIPTION

This disclosure, including the inventions herein, relates to implantable drug delivery devices. In some embodiments the drug delivery systems are integrated with capsular tension ring, which may be circular or arcuate. Capsular tension rings that are part of implanted devices herein can be configured and adapted for implantation into the capsule of a patient during a cataract extraction and intraocular lens implantation procedure.

Figure 1A:
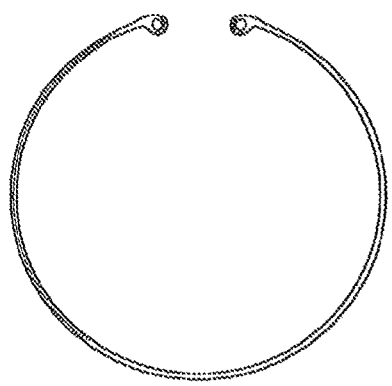
FIGS. 1A, 1B, 1C, 1D, 1E, 1F, 1G, 1H, 1I illustrate exemplary prior art capsular tension rings.
Figure 1B:
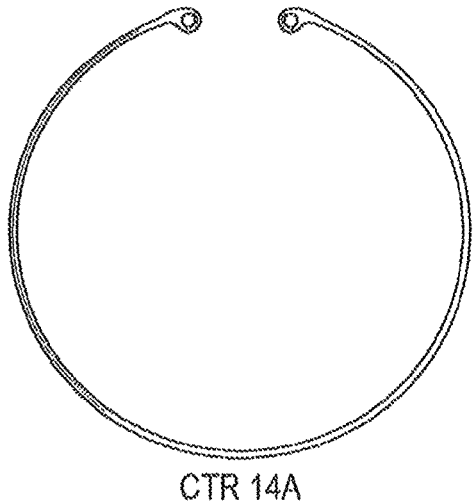
Figure 1C:
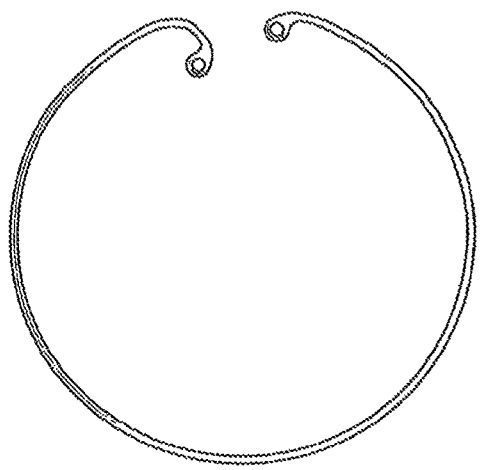
Figure 1D:
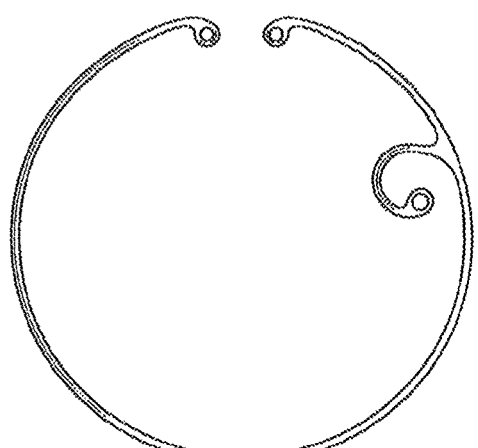
Figure 1E:
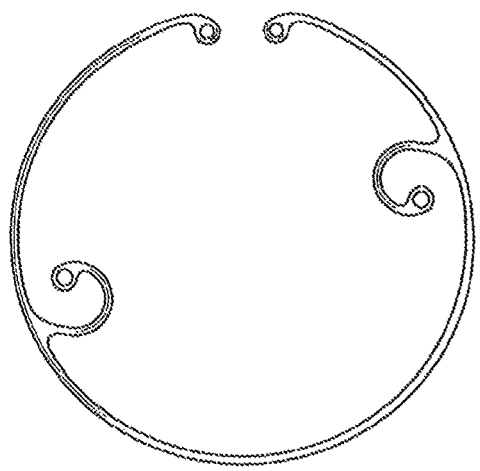
Figure 1F:
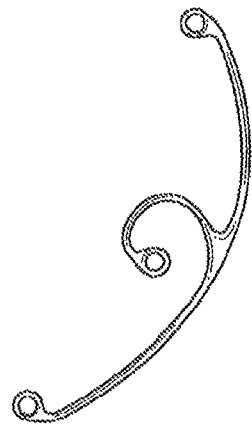
Figure 1G:
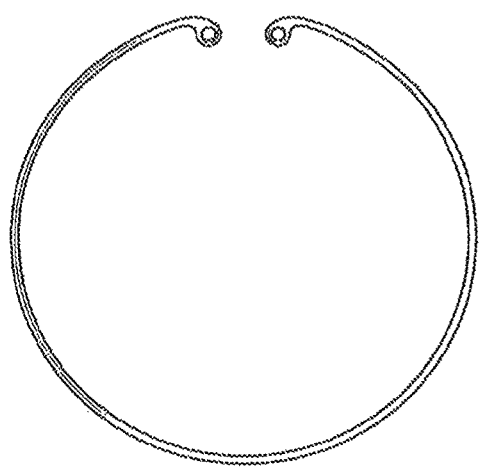
Figure 1H:
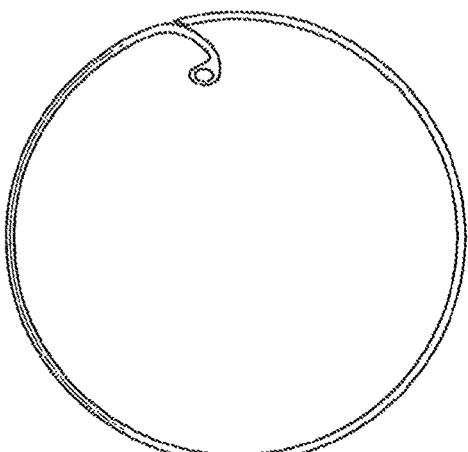
Figure 1I:
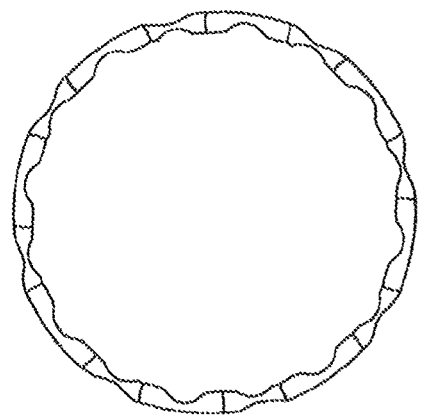

The capsular tension ring may not form a complete annular configuration, in which case the capsular tension ring has at least two free ends (see, e.g., FIG. 1A).

Any of the implantable devices herein can include at least one drug depot containing a drug formulation in either a solid or liquid form, or both, that releases drugs at a controlled rate to the eye. The drug depot can preferably be a stand-alone structure that is connected (e.g., tethered) to or integrated with a capsular tension ring. The drug depot(s) are generally referred to as the location where the drug formulation is stored, and from which the drug is released into the eye.

The drug(s) contained within the one or more drug depots can be drugs that act to control elevated intraocular pressure. The depot(s) can contain drugs or drug formulations that have been approved for control of intraocular pressure, including, as non-limiting examples the following: Beta blockers such as Timolol that work by decreasing production of fluid; alpha agonists (e.g., Alphagan® P (brimonidine), Iopidine®) that work to both decrease production of fluid and increase drainage; carbonic anhydrase inhibitors ("CAI"s; e.g., dorzolamide, acetazolamide or brinzolamide) that act to reduce eye pressure by decreasing the production of intraocular fluid; rho kinase inhibitors, (e.g., netarsudil, Fasudi) which increase the drainage of intraocular fluid. The drug depots can also have combined medications, which can offer an alternative for patients who need more than one type of medication. For example, Cosopt® is a combination of a beta blocker (timolol) and a carbonic anhydrase inhibitor (dorzolamide) and is available in generic form and also as a preservative-free formulation (Cosopt® PF). Additionally, for example, Combigan® combines an alpha agonist (brimonidine) with a beta blocker (timolol). Additionally, for example, Simbrinza® is a beta blocker-free combination medication consisting of brinzolamide and brimonidine. Any of the drug depots herein can include combined medications. Any given drug depot can include more than one drug formulation, such as in separately controlled depot regions. Any of the systems herein can also include one or more drug depots that are located in different portions of the implant and are spaced apart from one another, in which case the different depot can include the same or different drug formulations.

Any of the depots herein can also contain medications required to provide immediate post-operative management of the wound healing process that may require hours of administration of drugs by instillation, particularly when compliance to the complicated protocols of drug administration are most challenging to patients.

Any of the depots herein may be made of a stable material with a biocompatible surface, or they may be made of an erodible material, such that it dissolves and disintegrates after the drug release has been completed. If the depots are made of a permanent material, the depots may be refillable. In those cases, the depots may be made of a rigid material such as Titanium or gold, or a flexible material such as, for example without limitation, a cross-linked hydrophobic polymer. Polymeric depots are generally further coated with a barrier film such as multiple layers of SiOx/Paralyne C, as provided by Coat-X corporation, in order to prevent any diffusion through the body of the depots.

The depots herein are provided with drug release regions, which are regions that are adapted to release the drug(s). The drug release regions may include porous hydrophilic membranes with a controlled pore size. Preferably, the drug release regions are made of a hydrophilic polymer such as a hydrogel, with holes in them created by copolymerizing hydrophobic pendant groups soluble in hydrophobic solvents, then removing these pendant groups subsequent to forming of the membrane. The size of the holes in the hydrogel membrane may be controlled and adjusted to be in a size range such as, for example, 50 nanometers to 1000 nanometers, preferably 100 nm to 500 nm. Holes in this range will allow ready diffusion of the aqueous humor into the depot and release of drug formulations from within. In some preferred embodiments, the depot itself is constructed of an erodible polymer, such as poly lactic-co-glycolic acid (PLGA). The wall thickness of the depot may be selected so that it retains its integrity until after drug release is completed. A preferred range of the time over which drug release is completed is from about 100 hours to about 6 months/4, 500 hours. This broad range of time is due to the fact that antibiotics delivered intraocularly are mainly needed over a range of 24 hours (1 day postoperatively) to 168 hours, while steroids and NSAIDs delivered postoperatively will be required for a period of 100 hours to 1000 hours, while anti-glaucoma medication will be required on an ongoing basis.

In some preferred embodiments, the drug delivery systems can include a titanium vessel containing up to 1 mL of a drug formulation.

Any of the drug depots herein can be connected (e.g., mechanically, electrically or magnetically) in an operable manner with a hermetically sealed electronic module, which may contain or is in communication with an antenna.

The electronic module can include one or more sensors. Any of the one or more sensors herein can be a sensor of a physiological parameter that indicates a need for a drug to be delivered by the depot and/or correlates with the concentration of the drug being delivered by the depot. For example, the one or more sensors can be an intraocular pressure sensor that is adapted to sense intraocular pressure, which can be indicative of a need for a drug to be delivered from the depot. For example, if an IOP sensor senses a higher that desired pressure, the sensed information can be indicative of a need for a drug to be released from the drug depot. Additionally, for example, any of the sensors herein can be adapted to sense another parameter that is indicative of or correlated with an IOP.

Any of the sensors herein can be a chemical sensor that is adapted to sense a, for example drug that is being delivered by the one or more depots, or one or more biomarkers that is indicative of a drug concentration and/or indicative of a physiological parameter that is indicative of or correlated with a need for the drug to be delivered from the depot.

Regardless of the type of sensor, the one or more sensors herein can be controlled by and/or in communication with any of the following: an electronic control and actuation module, a battery that is optionally rechargeable, a flash memory and optionally an EEPROM, and an RFID module including its own antenna and firmware.

Any of the implantable devices herein can be adapted to be in communication (constant or periodic, or some combination thereof) with an external unit that is configured to wirelessly communicate with the implantable device, and may provide wireless energy and data transfer from and to the implantable device. The disclosures herein include optional remote database(s) that can be adapted to do any of the following: receive data from an external unit, store drug concentration data, and provide access to the data or analysis thereof to caregivers and others as needed.

Figure 4:
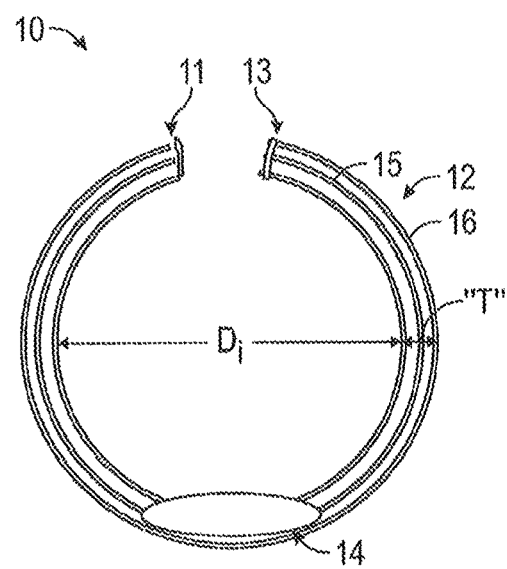
FIG. 4 illustrates an exemplary implantable drug delivery device that is adapted to also function as a capsular tension ring.

FIG. 4 illustrates an exemplary side view of an exemplary implantable drug delivery device that is also configured and adapted to function as a capsular tension ring. Device 10 includes an arcuate body 12 (which in this embodiment has a partially annular configuration) and a drug delivery device 14. The partially annular body 12 includes first end 11 and second end 13, which together form two free ends. In alternative designs, the partially annular body could be replaced with an annular body, which would not have free ends. Partially annular body 12 includes antenna 15, which has a partial loop, or ring, configuration, and a coating layer 16 that is disposed on antenna 15. Antenna 15 is in operable communication with drug delivery device 14, which provides functionality described below. In FIG. 4, drug delivery device 14 and partially annular body 12 are integrated into a single hermetically sealed system. As set forth above, the drug delivery device includes at least one depot, and can include other components such as an electronic module, one or more sensors, etc.

When the phrase "arcuate body" is used herein, it is intended that this phrase includes at least partially annular bodies and annular bodies.

Figure 5:
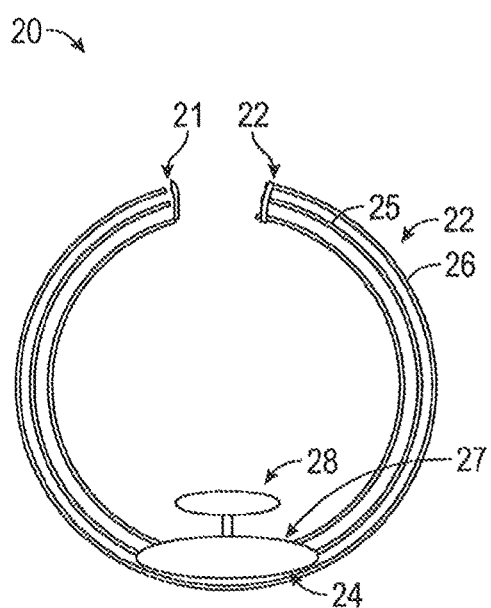
FIG. 5 illustrates an exemplary implantable drug delivery device that is adapted to also function as a capsular tension ring.
Figure 2:
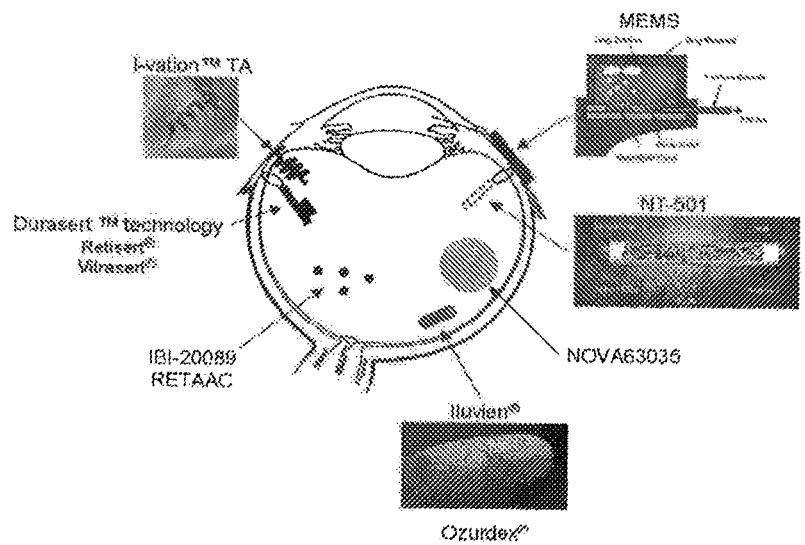
FIG. 2 shows examples of existing intravitreal drug delivery systems for vitreoretinal diseases.
Figure 3:
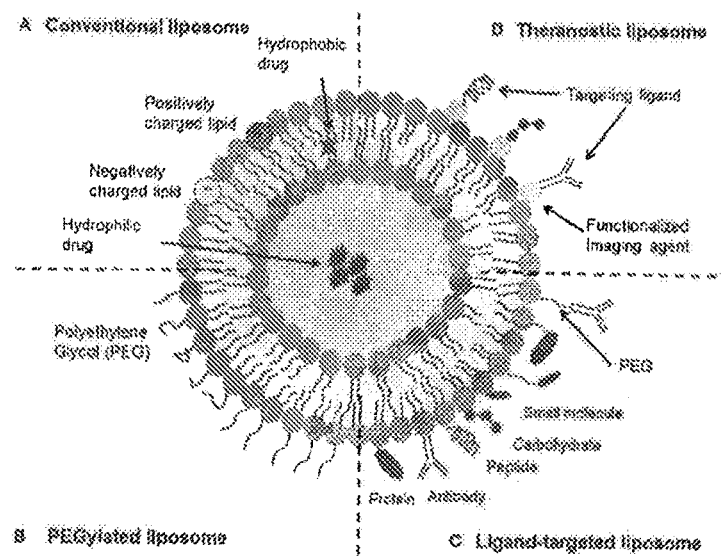
FIG. 3 illustrates a liposome based drug delivery formulation, which may be optimized for retention and delivery of both hydrophilic and hydrophobic drugs.

FIG. 5 illustrates an exemplary implantable drug delivery device that is also configured and adapted to function as a capsular tension ring. Device 20 includes an arcuate body 22 (which in this embodiment has a partially annular configuration) and drug delivery device 24. The partially annular body 22 includes first end 21 and second end 23, which together form two free ends. In alternative designs, the partially annular body could be replaced with an annular body, which would not have free ends. Partially annular body 22 includes antenna 25, which has a partial loop, or ring configuration, and a coating layer 26 that is disposed on antenna 25. Antenna 25 is in operable communication with electronic drug delivery device 24, which provides functionality described below. In device 20, drug delivery device 24 includes electronic module 27 and drug depot 28. Drug depot 28 extends outward from the generally annular configuration of arcuate body 22.

As set forth above, the arcuate body preferably comprises materials and thicknesses that provide physical properties that resemble existing capsular tension rings. This means that the material and dimensions of the antenna and coating layers are chosen that will provide the desired physical properties for the annular body.

The coating layers herein may be made of a silicone or acrylic elastomer, for example, silastic rubber or a copolymer of acrylates and methacrylates, cross-linked in order to preserve a an arcuate shape. In some preferred embodiments, the coating layers here are made of a cross-linked copolymer of acrylates and methacrylates. Its glass transition temperature can preferably be less than 10 C, and can be in the range 0 C to 10 C, so that the coating layer or layers are elastomeric during use at normal eye temperature (35-38 C).

The enclosed antennas herein act as a stiffener for the arcuate body, therefore use of PMMA for the coating layer should be generally avoided when constructing the arcuate bodies of the devices here. The thickness of the applied coating and the material composition (including, without limitation, its glass transition temperature and its tensile and bulk moduli) are adjusted so that the spring constant of the resulting CTR does not exceed 4 mN/mm.

Preferably, the antenna with its substrate make a snug fit with the surrounding elastomeric layer, which together make up the structure that functions as the CTR, so that there is no free space between the antenna and the coating layer that may otherwise accumulate moisture or aqueous humor.

In some preferred embodiments, the modulus of the arcuate body portion of the device should be in the range 1-10 MPA, and its elongation at break should be in the range 50-150%. The spring constant of the arcuate body portion, including the enclosed antenna, should be in the range 2.00-4.00 mN/mm.

In some embodiments, the arcuate body is formed by first making (e.g., casting) a hollow tubular element out of, for example, an acrylic or silicone elastomer, then advancing the antenna inside the formed hollow tubular element. The tubular element and antenna are sized such that the antenna makes a snug fit with the inner surfaces of the hollow tubular element. The device can have an internal diameter "D" (see FIG. 4) in the range 10.0-15.0 mm, more preferably 11.0 mm to 14.0 mm. The wall thickness of the at least partially annular body should be in the range of 0.1 mm to 0.25 mm. The internal diameter of a hollow tubular element (if that is incorporated in the at least partially annular body) should be in the range of 0.1 mm to 0.20 mm.

In some preferred embodiments, the drug delivery devices herein can be hermetically sealed in a Titanium casing of thickness not exceeding 50 microns, and preferably in the range of 10-15 microns. The pressure sensing units can be encased in a multilayer coating comprised of $SiO_x$ and Paralyne (preferably Paralyne C), and is immersed in a substantially low viscosity liquid medium inside the hermetic seal. Preferably, the number of layers of coating applied is more than five, and the coating is in the range of 5-100 microns. Preferably, each such layer has a thickness of 5-100 nanometers. Preferably, the viscosity of the medium in which the sensor is immersed should not exceed 1000 cst at room temperature, and more preferably in the range 50-500 cst at 25 C. The hermetically sealed electronics package and the sensor of any of the sensors are preferably overcoated with a thin layer of the same copolymer material that is used to coat the antenna, so that there is no weld or adhesive joint between the at least partially annular body and the drug delivery device.

In some preferred embodiments, the entire device, including the at least partially annular body and the electronics, is coated with a highly biocompatible coating that prevents cellular deposition and minimizes fibrosis. Preferably, this coating is a hydrophilic cross-linked acrylate and/or methacrylate, made of polyethylene glycol segments.

Any of the sensors herein can be, for example, an intraocular pressure sensor, which can be, for example, piezoresistive or capacitative. The drug delivery devices can also include a microcontroller or an ASIC with embedded firmware to provide electrical control functions. The drug delivery device can also include a real time clock, a voltage converter, a rechargeable battery, optionally a thin film solid state rechargeable battery. A rechargeable battery may either be integrated into one hermetically sealed package or multiple sealed packages connected by electrical wires conveyed into each such package by vias (see, for example, FIG. 5). The drug delivery device can also include a flash memory and an EEPROM. The drug delivery device can be thought of as being in operable communication with the antennas herein, even though the antennas herein can be thought of a part of the overall implantable device. The drug delivery device can also include one or more elements adapted to wirelessly transfer data and power to and from the implantable device to an external device. The electronics module comprising a sensor may be controlled and operated by firmware that includes embedded algorithms stored in the EEPROM memory unit of the pressure sensor. Optionally, the firmware is reprogrammable via wireless means remotely by an external unit.

Figure 6:
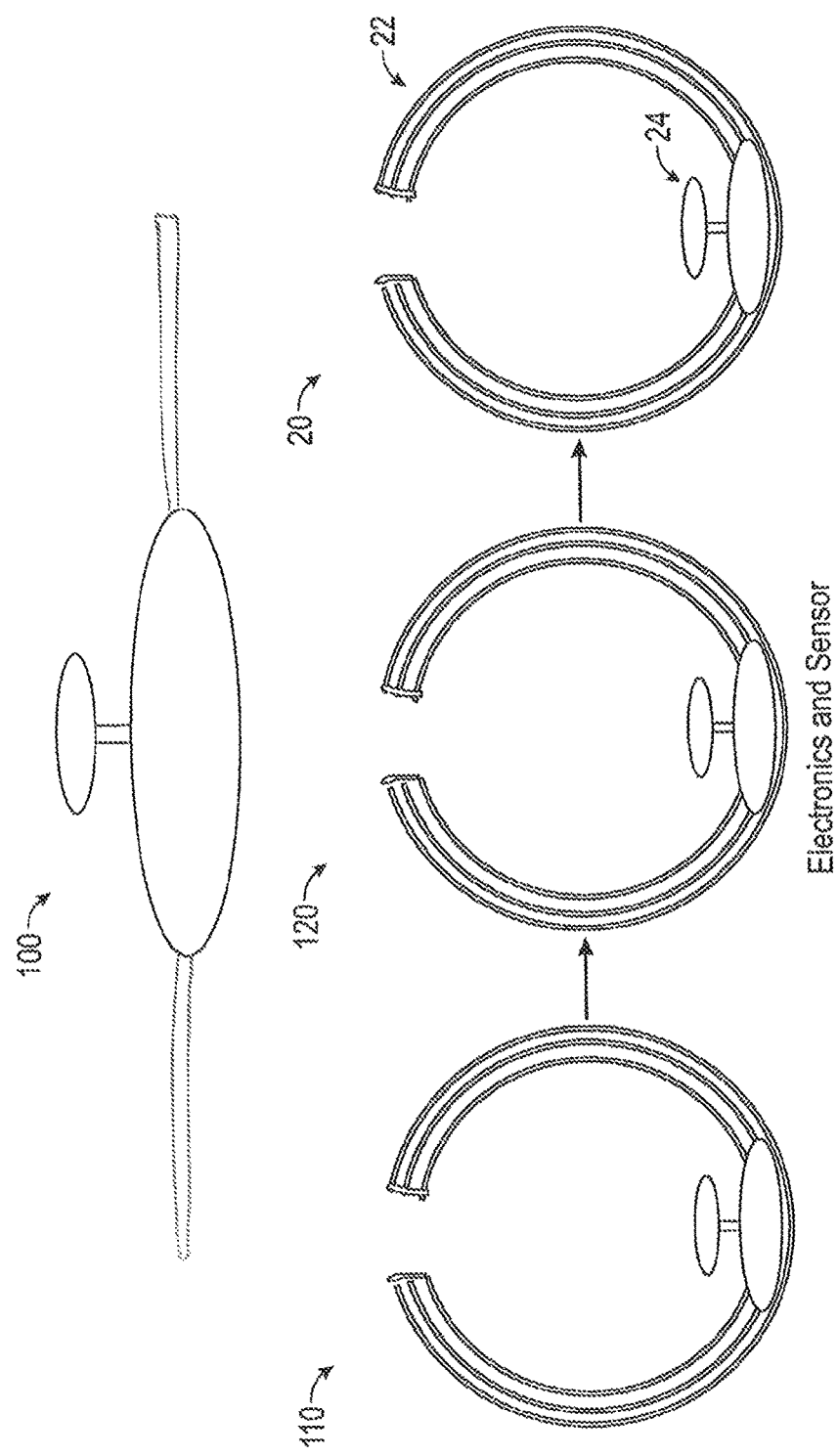
FIG. 6 is an exemplary method of manufacturing an implantable drug delivery device that is also adapted to function as a capsular tension ring.

Exemplary Manufacturing Processes. There are several methods that can be used to fabricate the implantable devices herein, including, for example, 3D printing, cast molding, injection molding, machining, etc. A merely exemplary process to make the device from FIG. 5 is illustrated in FIG. 6. In this approach, the drug delivery device and antenna 100, fabricated initially with straight antennas, is coated with a polymer that includes acrylates and methacrylates. This coating step can be accomplished by dipping or spraying the device with a mix of monofunctional acrylates and methacrylates and an initiator, so that an elastomeric coating is formed that remains uncross-linked. An uncross-linked coating has no shape memory, so it can be bent and shaped into the configuration as shown as device 110. A mix of a difunctional, trifunctional or tetrafunctional monomers and a UV photoinitiator is then sprayed on top of the uncross-linked coating, and the mixture is allowed to diffuse into the bulk of the coating. Device 110 is then exposed to actinic UV radiation, exposure to which activates the initiator, and initiates cross-linking. When the cross-linking process is completed, the shape of the at least partially annular body is now set, as shown as device 120. The cross-linking process can thus be used to set the configuration of the at least partially annular body. A biocompatible coating is then applied to device 120, resulting in device 20.

The optional two-step polymerization and forming process illustrated in FIG. 6 ensures that there is no free space between the inner wall of the coating layer and the antenna, which ensures there isn't any space for moisture or aqueous humor to accumulate.

The shaped antenna and coating thus provide capsular tension ring functionality to the implantable device, and the drug delivery device 24 can includes a sensor. A monomer application process, including without limitation, spraying, dipping or 3D printing is selected that provides the required level of uniformity in thickness of the coating prior to being polymerized in place. Variation in thickness (outer diameter)

of the coating layer of up to +/−30% is generally acceptable, preferably being 200 microns+/−30%.

Any of the antennas herein can be made of gold, gold coated Nitinol, or gold-coated copper, and can have a thickness in the range of 25-100 microns. The antennas can have a circular cross section.

The thickness of the polymeric coating layer can be in the range of 40-235 microns, preferably in the range of 75-200 microns.

Table 1 provides examples of monomer compositions used in the exemplary process described with reference to FIG. 6.

| Exemplary Manufacturing steps | Exemplary monomer compositions |
| --- | --- |
| Uncross-linked coating formation | Isobutyl acrylate, ethyl acrylate, phenyl acrylate, phenoxyethyl acrylate, isobornyl acrylate, ethyl methacrylate, photoinitiators that initiate free radical polymerization including benzophenone derivatives, acetophenone derivatives, phosphine oxide derivatives, including TPO, TPO-L |
| Cross-linking coating to form at least partially annular body | Ethylene glycol dimethacrylate, bisphenol A Diacrylate, trimethylene propane triacrylate, pentaerythritol tetracrylate, TPO, TPO-L |
| Biocompatible coating formation | Ethylene glycol Diacrylate, ethylene glycol dimethacrylate, TPO, TPO-L |

The implantable drug delivery devices herein can be adapted to communicate with an external unit capable of communicating with the implant wirelessly. The external unit can be adapted so that the external device can provide wireless energy transfer from and to the implant, can be capable of downloading sensed data (e.g., sensed IOP data) from the implant, can be adapted to perform data processing, can store data on board, and can be adapted to transmit the data to a database, optionally established in a cloud based server.

Any and all aspects of the implantable pressure sensing devices and methods of manufacture described in PCT publication WO2017/210316 are fully incorporated by reference herein for all purposes, and can be incorporated into any of the suitable implantable pressure sensors and method of manufacture herein.

The drug delivery devices herein can include one more drugs, and they can be a desire or need that the different drugs be released at varying rates. For example, anti-inflammatory agents, and fibrinolytics to control blood clotting and fibrosis leading potentially to angle closure, can be particularly required for diabetic patients, may be required for up to 6 months post-surgery. This disclosure thus contemplates techniques, strategies, and designs that can be used to control or achieve a variety of drug release rates.

Figure 7:
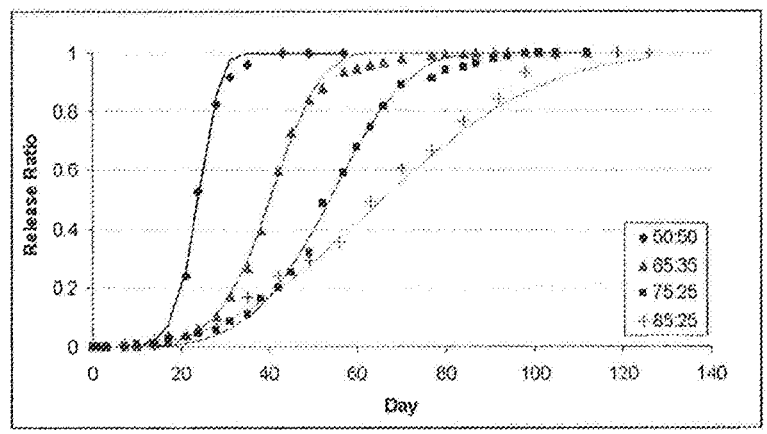
FIG. 7 illustrates the drug release rates from a series of PLGA Copolymers, in which the percentage of lactic acid varies from 50% to 85%.

This disclosure highlights three non-limiting strategies that can be used to achieve a wide dispersal of drug release rates. In some embodiments, a drug formulation inside the depot includes an aqueous solution of drugs that are to be delivered immediately upon wound closure, as well as nano and micro-particles incorporating drugs that are required to be delivered over a longer period. In a merely exemplary illustration of this concept, nano and microparticles of PLGA, a biocompatible, erodible polymer may be used as a drug carrier. Makadia, et al have shown that the release rate and degradation rate of the copolymer strongly depends on the mole fraction of lactic acid in the copolymer. FIG. 7 illustrates the drug release rates from a series of PLGA Copolymers, in which the percentage of lactic acid varies from 50% to 85%, which is reproduced from Makadia, H. K., et al. The incorporated drug may be surface bound on the particles of PLGA (or other particle), or it may be incorporated in the bulk of the particles, or even a fraction of the total load of the drug may be on the surface of the particles with the remainder of the drug load being incorporated into the bulk of the carrier particle. The distribution of the drug depends on its hydrophobicity, and whether it can bind to the carboxylic groups in the surface of the particle.

An additional way of controlling the drug release rate is by further incorporating the target drugs into a hydrophilic hydrogel matrix such as a polyethylene glycol based hydrogel or a Chitosan based hydrogel, depending on the affinity of the specific drug target to the pendant groups of the hydrogel, then enclosing this hydrogel micro or nanoparticle within a shell of PLGA, a hydrophobic, erodible matrix.

In a preferred embodiment, constituents of the targeted drug formulation that require relatively immediate release will be provided in the form a preserved or non-preserved solution in a solvent carrier such as physiological saline, or a phosphate buffered saline solution, while constituents that require extended release will be incorporated in a nano or micro-particle of an erodible biocompatible polymer, such as by example only, PLGA. Two or more configurations of the nano- or micro-particles will be used, varying in size or composition. A third type of carrier particle can also be employed, in which the hydrophilic drug is incorporated into a hydrogel core particle, over-coated with a shell of an erodible polymer. The release rates and timing of the different constituents can thus be controlled, depending on the need and timing of the release.

In some embodiments, some of the nano or micro-particles will be transported into the aqueous humor through the one or more holes in the release zones of the depot, while other particles will continue to release drugs within the depot, which are then transported outside the depot through the one or more holes. This mechanism of drug delivery places an upper limit to the size of nano or micro-particles, since it will not be desirable for the particles to block the trabecular meshwork or the angle. This limit is recognized to be approximately 5 microns (~5000 nm).

In any of the drug delivery devices herein, drug delivery from a depot may be controlled by being switchable between release states (or configurations) and non-release states (or configurations). The mechanism of electronically controlled drug delivery may be selected from a number of options, including, for example without limitation, a piezoelectric driver, a bubble actuated process driven by electrolysis, an electrowetting mechanism, a peristaltic MEMS pump, an electromagnetic actuator, or a linear drive driven by a potentiometer. In a preferred embodiment, the depot is enclosed in an outer container or jacket that blocks the drug delivery zones of the depot. This outer jacket can be translated to expose the drug delivery zones to the circulating aqueous humor, using an actuator for example. Mechanical translation of the jacket can be controlled in order to expose only a fraction of drug releasing sites, thus providing finer control of the rate of release of drugs.

Any of the techniques described above for controlling drug release rate and for controlling the release of two or more constituents can be utilized in any of the drug delivery systems herein.

Sensors and Electronic Module. As set forth above, any of the drug delivery devices can includes one or more sensors. The one or more sensors may be adapted to monitor any of the following, including any combination thereof: intraocular pressure, concentration of drug molecules being released by the drug delivery device, and critical biomarkers in the aqueous humor that may be indicators of onset of glaucoma or other systemic eye diseases, such as uveitis.

Figure 8A:
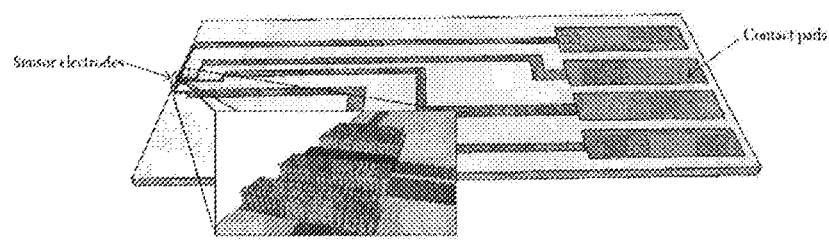
FIGS. 8A and 8B show an example of a microelectrode patterned with silicon nano-towers.
Figure 8B:
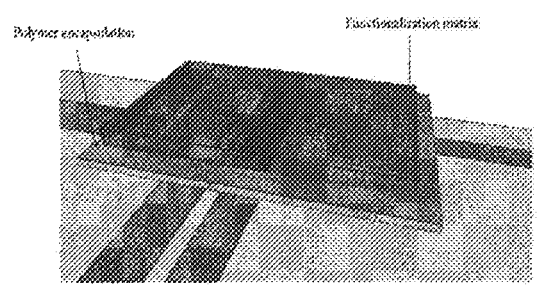

In some embodiments, a sensor may be an electrochemical sensor, for example, including an ion specific electrode, surface modified to bind specifically with one or more target analytes. The electrode is preferably patterned in order to increase surface area of the electrode that both serve to reduce electrode resistance and increase the loading of target analytes on its surface. FIGS. 8A and 8B show an example of a state of the art microlectrode patterned with silicon nano-towers. FIGS. 8A and 8B show a micro-patterned sensor electrodes for electrochemical sensing, and is reproduced from Mujeeb U-Rahman, M., et al, "Fabrication of Patterned Integrated Electrochemical Sensors', Journal of Nanotechnology, 2015; Article ID 467190. The surface of an electrochemical sensor can be modified to bind specifically with one or more chosen analytes. Preferably, the electrode is coated with or bonded to a polymer with pendant groups that preferentially attach to a target analyte, such as a drug molecule. The polymer chain also has a molecule that functions as redox couple, in other words, can reversibly undergo an oxidation and reduction (gain or loss of one or more electrons) reaction when a particular bias voltage is applied to the electrode that matches its oxidation or reduction potential. The redox potential of the redox couple is altered when a drug molecule becomes attached to the polymer layer, and it is this altered voltage (which can be measured) that provides an indication of the presence of the drug molecule. A quantitative measure of the concentration of the drug molecule in the aqueous humor circulating around the electrochemical sensor can thus be derived by performing a coulometric or a cyclic voltammetric measurement.

For continuous monitoring capability, the electrochemical cell can be driven through a voltage cycle that drives a redox process (e.g., protonation or deprotonation) of the drug molecule bound to the surface of the polymer bound to the electrode surface, causing a debonding of the attached drug molecule, thus freeing up the active sites on the polymer coating on the electrode for further sensing.

A potentiometric scan that detects the presence of a target drug molecule followed by a coulometric scan that measures the quantity of the drug molecule is preferred to a measure of inductance or double layer capacitance as a function of frequency.

In some preferred embodiments, the drug delivery device or system includes an intraocular pressure sensor, operably connected to an electronic module that reads the sensor at specified intervals during the day, stores and preliminarily processes the data using algorithms and logic embedded in its firmware, stores the data in an on-board memory, and transmits the data wirelessly when programmed to do so, or when being interrogated by an external unit. It also recharges an on board rechargeable battery, and provides power for its own and the sensor's operation. Preferably such a pressure sensor is either a capacitative or a piezoresistive sensor. In a preferred embodiment, a pressure sensor is encased in a multilayer coating comprised of $SiO_x$ and Paralyne (preferably Paralyne C), and is immersed in a substantially low viscosity liquid medium inside the hermetic seal. Preferably, the number of layers of coating applied is more than 5, and in the range of 5-100. Preferably, each such layer is of thickness 5-100 nanometers. Preferably, the viscosity of the medium in which the sensor is immersed should not exceed 1000 cst at room temperature, and preferably in the range 100-1000 cst at 25 C.

In some embodiments that include a pressure sensor, the electronic module obtains data from the pressure sensor or the electrochemical sensor, processes the data and compares the data to values stored in one or more look up tables, then sends an actuation signal to activate the drug delivery system, if warranted. Computer executable methods can be incorporated to perform any of these methods or any of the algorithms herein.

In preferred embodiments, the one or more sensors and the drug depot are outside of the hermetic seal that surrounds and encloses the electronic module (see the bottom of FIG. 5). In these embodiments, the sensor(s) and the depot are mounted in a pedestal and connected to the electronic module via a bus that is connected to the electronic board through a via.

The sensor(s) and the depot can be separately mounted at any location on the capsular tension ring, and electrically connected to the electronic module via a bus that runs alongside the antenna.

Figure 9:
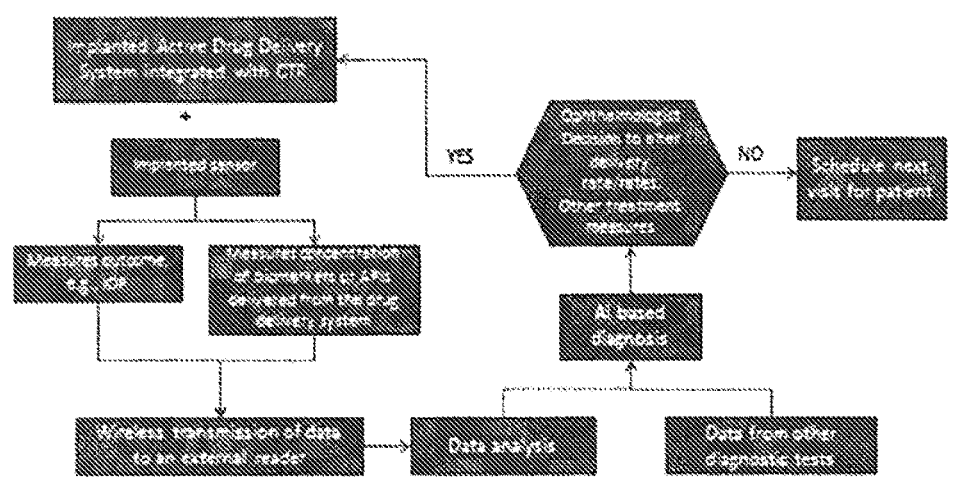
FIG. 9 illustrates an exemplary method of drug delivery.

The drug delivery systems herein can include a closed loop system that includes the one or more sensors (and information/output sensed by them) and delivery of the one or more drugs. This allows output from the one or more sensors to be used to directly modulate or control the rate of drug delivery from the depot(s), including stopping drug delivery altogether. This feedback loop can include an external reader comprising a memory element that can be adapted to perform one of more of the following: collect the data from the one or more sensors, combine it with other diagnostic data that may have been gathered by the caregiver, perform a deep analysis of the disease state of the patient, arrive at a diagnosis, and make a decision whether to alter the drug delivery rate based on this diagnosis. The results of the computerized analysis of the disease state and the subsequent diagnosis can be reviewed by the caregiver and altered, modified or rejected altogether. In these closed loops, the caregiver can affect and control the operation of the system either through direct intervention at the point when the trigger to alter the state of the drug delivery system is about to be reset, or at the point where the analysis of the disease state has been made by one or more computer executable methods that preferably utilize artificial intelligence to complete the analysis. An exemplary flowchart showing an exemplary method is shown in FIG. 9. Not all steps need to be part of the exemplary method. In the exemplary method of FIG. 9, the implanted sensor is adapted to measure both IOP and either biomarkers or drugs, but the method can include sensing from only one kind of sensor, for example. Additionally, for example, data from other diagnostic tests need not be included in the method. These closed loop systems are generally referred to herein as "active drug delivery systems.

Figure 10:
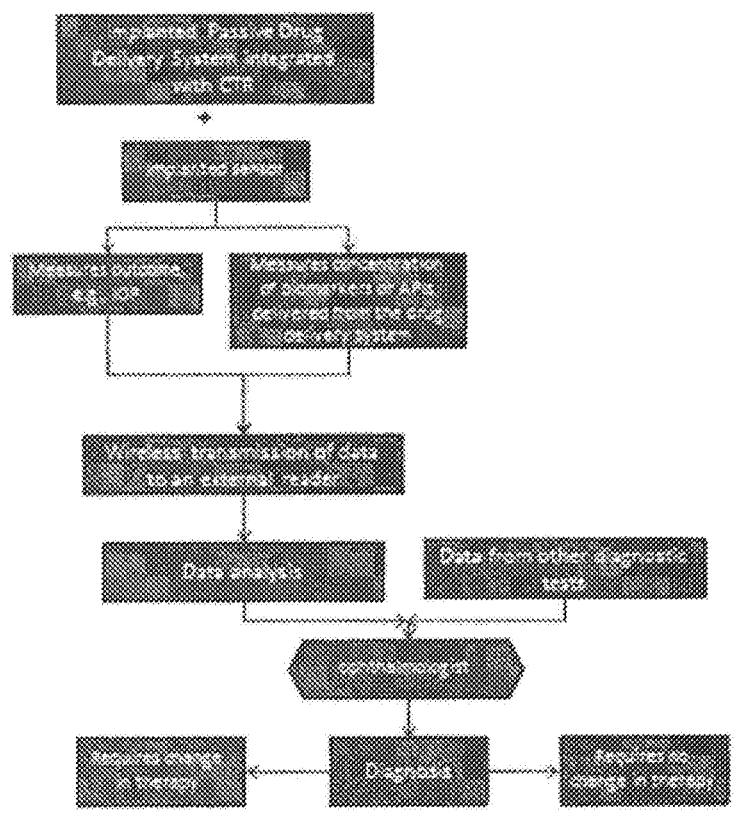
FIG. 10 illustrates an exemplary method of drug delivery.

FIG. 10 illustrates an alternative type of system and method herein referred to as "passive" drug delivery. In passive drug delivery systems, a direct feedback loop to the implanted drug delivery system is not included, but the physician can still review the data analysis and make a decision about whether to change the therapy or not.

In any of the embodiments herein, the capsular tension ring can have a complete annular configuration, or it can have a plurality of free ends. In any of the embodiments in which it has a closed configuration, the structure can include one or more regions that have relatively greater flexibility or flexure than the remainder of the tension ring, such as for example, one or more regions that have any of the following configurations: springs, coils, wavelike, indentations, bends, etc. The one or more regions of increased flexibility accommodates patient to patient size variability, and allows a complete annular structure to bend, flex, or deform at one or more of the localized regions to accommodate forces that might act on the structure from tissue in the eye. These types of devices can thus be more adaptable over a greater number of patients.

Several points of fixation for the drug delivery system and optional sensor(s) have been disclosed herein. A preferred location for these components is within or on the capsular tension ring. This is because the capsular tension ring is typically implanted along the capsular equator, so that the depot and the sensor are similarly and beneficially outside of the light path to the pupil and the retina. In this location they are also safely out of the way of uveoscleral tissue that can develop inflammation upon contact with the implanted device, for example, the iris, the corneal endothelium, or the trabecular meshwork. Integrating a drug delivery system with a capsular tension ring device thus provides significant benefits it does not interfere with the light passing the retina, and minimizes the occurence of inflammation of uveoscleral tissue.

The invention claimed is:

1. An intraocular implant, comprising:
   an implantable intraocular drug delivery system integrated with a capsular tension ring, the capsular tension ring sized and configured for implantation into at least one of the capsule and the ciliary sulcus of humans and/or canines,
   wherein the capsular tension ring comprises at least one drug depot, at least one sensor, an electronic module, and an embedded antenna,
   wherein the at least one sensor is sized and configured to sense at least one of intraocular pressure (IOP), a drug that is part of a drug delivery program that is being administered to a patient, and a biomarker indicative of intraocular pressure or other disease state,
   wherein the at least one sensor is operably connected to the electronic module, whereby the at least one sensor is adapted to provide electronic data to the electronic module,
   wherein the at least one sensor is adapted and in communication to provide data that is used to modify the rate of release of drugs from the at least one depot,
   wherein a spring constant of the capsular tension ring is in the range of 2.00 mN/mm-4.00 mN/mm,
   wherein said capsular tension ring is sized and configured to contact the capsular equator and to provide improved centration of an intraocular lens that is sized and configured to be implanted during the same surgical procedure.

2. The implant of claim 1, wherein said at least one sensor is hermetically sealed in a multilayer coating of SiOx and Paralyene C, wherein each such layer of SiOx and paralyene C is of thickness in the range 10-500 nm.

3. The implant of claim 1, wherein said at least one sensor comprises an electrochemical sensor.

4. The implant of claim 1, wherein said at least one sensor comprises an intraocular pressure sensor.

5. The implant of claim 1, wherein the at least one depot contains at least one of the following drugs: Timolol, Alphagan® P (brimonidine), Iopidine®, dorzolamide, acetazolamide or brinzolamide, netarsudil, Cosopt®, Cosopt® PF, Combigan®, Simbrinza®, cefuroxime, levofloxacin, and moxifloxacin, and nepafenac or bromfenac.

6. The implant of claim 1, wherein the at least one depot comprises at least one of the following drug formulations: saline, physiological saline, or a buffered saline; a blend of a drug with poly lactic-co-glycolic acid copolymer nano or micro-particles; and a blend of a drug with a hydrogel matrix coated with a shell of a lactic-co-glycolic acid copolymer.

7. The implant of claim 1, wherein the at least one depot comprises an erodible material.

8. The implant of claim 1, wherein the capsular tension ring comprises a cross-linked polymer of glass transition temperature in the range 0 C to 10 C.

9. The implant of claim 1, wherein the implant is coated with a biocompatible coating.

10. The implant of claim 1, wherein the capsular tension ring is arcuate in design, allowing the ring to be implanted into a wide range of capsules in human eyes.

11. The implant of claim 1, wherein the capsular tension ring is made of a cross-linked polymer that retains shape memory.

* * * * *